United States Patent [19]

Bennett, Jr. et al.

[11] Patent Number: 4,511,534

[45] Date of Patent: Apr. 16, 1985

[54] LIQUID TRANSFER DEVICE

[75] Inventors: John T. Bennett, Jr., 10087 Tyler Pl., Ijamsville, Md. 21754; Jack E. Goodman, Germantown, Md.

[73] Assignee: John T. Bennett, Ijamsville, Md.

[21] Appl. No.: 382,335

[22] Filed: May 26, 1982

[51] Int. Cl.³ .............................................. B01L 3/02
[52] U.S. Cl. ................................. 422/100; 73/863.32; 73/864.11; 141/238; 141/245; 222/263
[58] Field of Search ...................... 422/100; 73/863.32, 73/864.11, 864.24, 864.15; 141/238, 245, 24–27; 222/214, 263, 269, 276; 215/341

[56] References Cited

U.S. PATENT DOCUMENTS

| | | | |
|---|---|---|---|
| 888,818 | 8/1908 | Karrmann | 215/343 |
| 963,517 | 7/1910 | Coll | 215/341 |
| 2,517,796 | 8/1950 | Mathis | 73/864.11 |
| 2,538,695 | 1/1951 | Mathis | 73/864.11 |
| 2,595,493 | 5/1952 | Slaby et al. | 422/100 |
| 3,312,255 | 4/1967 | Miller | 141/24 |
| 3,430,628 | 3/1969 | Wiggins | 73/863.32 |
| 3,433,380 | 3/1969 | Kawchitch | 215/343 |
| 3,568,735 | 3/1971 | Lancaster | 422/100 |
| 3,572,552 | 3/1971 | Guinn | 422/100 |
| 3,650,306 | 3/1972 | Lancaster | 422/100 |
| 3,788,510 | 1/1974 | Collins | 215/341 |
| 3,807,235 | 4/1974 | Lefkovits et al. | 73/863.32 |
| 3,855,868 | 12/1974 | Sudvaniemi | 73/863.32 |
| 3,982,438 | 9/1976 | Byrd | 73/863.32 |
| 4,047,438 | 9/1977 | Sekine | 73/863.32 |
| 4,142,633 | 3/1979 | Raghavachari et al. | 422/100 |
| 4,158,035 | 6/1979 | Haase et al. | 422/100 |

FOREIGN PATENT DOCUMENTS 22002  10/1910  Norway ............................... 215/341

*Primary Examiner*—Steven Weinstein
*Attorney, Agent, or Firm*—Sughrue, Mion, Zinn, Macpeak and Seas

[57] ABSTRACT

The liquid transfer device includes a one-piece molded barrel plate having a plurality of syringe-type barrels extending downwardly therefrom and support flange extending downwardly about the perimeter of the barrel plate. An elastic membrane rests on and is substantially coextensive with the upper surface of the barrel plate. A retaining plate having a plurality of apertures in alignment with the respective barrels is detachably mounted on the barrel plate in either a first position wherein annular projections about each aperture lightly engage the membrane to hold it in place or a second position wherein the projections extend into each barrel to seal the membrane about the upper edge of each barrel. A plunger having a plurality of pins is placed on the retaining plate with the pins extending through the apertures to engage the membrane. Depressing and releasing the plunger will draw a predetermined amount of liquid into each barrel. The barrel plate, membrane and retaining plate can be packaged with or without a plunger as a sterile liquid transfer device.

4 Claims, 6 Drawing Figures

LIQUID TRANSFER DEVICE

BACKGROUND OF THE INVENTION

The present invention is directed to a liquid transfer device wherein a plurality of pipette-type devices can simultaneously pick up predetermined quantities of liquid from a suitable source and dispense the same into a plurality of individual receptacles.

Many tests and applications in the medical field require picking up predetermined amounts of liquid reagents from one container and injecting or depositing the same into another receptable or container as a daily or routine testing procedure. An example of such a test is one performed in a multi-well microtube tray where a culturing/rehydrating medium is added to a dried prepared microtube tray to perform an antibiotic sensitivity test or bacterial identification.

In the past, pins or prongs such as disclosed in the U.S. Pat. No. 2,956,931, to Goldberg, or loops as disclosed in the U.S. Pat. No. 4,115,200, to Anderson, were used for picking up small drops by surface tension and depositing them in another solution. The amount of liquid transferred by such means is generally limited and such means basically carry on a mixing operation because they take out the same volume they put in. The risk of contamination is high due to the contact of the prong or loop with the various mixtures in the containers. These drawbacks can be overcome by a positive displacement device such as a syringe. However, syringes generally require the use of O-rings or other close tolerance type seals which provide restraint to movement making them hard to operate when grouped into a multiple syringe device. Furthermore, use of such syringes is apt to be trouble prone as they can be easily contaminated, expensive or bulky.

The U.S. Pat. No. 3,982,438, to Byrd, discloses a multiple channel pipetting apparatus wherein a plurality of small tubes extend downwardly with the upper end portions communicating with reservoirs that have a predetermined volume. A flexible diaphragm extends across all of the reservoirs and the upper portions thereof are in communication with a common manifold chamber. The application of positive or negative pressure moves the diaphragm downwardly and upwardly into contact with the lower and upper reservoir walls respectively to either expel liquid from or draw liquid into the tubes. The accuracy of the amounts of liquid extracted or expelled by the tubes is dependent upon the pressure in the manifold chamber and the volume thereof and does not rely upon the use of reciprocating plungers.

The U.S. Pat. No. 3,568,735, to Lancaster, discloses a laboratory microtitration dispensing apparatus comprising a manifold connected to a plurality of passageways, a head member connected to the manifold and having a plurality of apertures aligned with the passageways but separated therefrom by a flexible diaphragm, an actuator mounted in each aperture including a piston normally biased by a spring to maintain the flexible diaphragm means out of its respective one of said apertures and a dispensing needle connected to each actuator assembly whereby, upon supplying and exhausting air to and from the manifold, the diaphragm will be moved by the differential pressure on opposite sides thereof to operate the pistons in the respective apertures to control the pick up and discharge of fluid by the needles. Thus, Lancaster utilizes air pressure in the manifold for controlling the transfer of liquid as does the patent to Byrd.

The U.S. Pat. No. 4,047,438, to Sekine, discloses a liquid quantitative dispensing apparatus for withdrawing liquid into a plurality of pipettes arranged in rows by simultaneously pressing and releasing cap-like projections formed of flexible material and dispensing the liquid to test tubes and the like. The cap-like projections of flexible material are disposed in alignment with a plurality of pipettes and extend upwardly into bores in a guide plate. A plurality of plungers secured to a common plate are operative within the bores for pressing on the cap-like projections to dispense liquid from the pipettes. In this patent, as well as the two previously mentioned patents, it is extremely difficult to provide a good seal for the membrane since the membrane is being clamped between two flat surfaces.

SUMMARY OF THE INVENTION

The present invention provides a new and improved liquid transfer device having a unique plunger and diaphragm arrangement in a multi-channel environment which provides for greater sensitivity and accuracy in operation as well as providing a unique sterile barrier.

The present invention provides a new and improved liquid transfer device comprised of a one-piece molded pipette plate having a plurality of pipette-type barrels extending downwardly therefrom with an annular upstanding boss surrounding the upper end of each barrel and a support flange extending about the perimeter of the pipette plate, an elastic membrane extending over and resting on each upstanding annular boss, a membrane retaining plate having a plurality of through passages, each of which is disposed in alignment with a barrel or pipette on said pipette plate and having a downwardly protruding boss surrounding each aperture and adapted to extend into the respective upstanding boss on said pipette plate and connecting means adapted to maintain said retaining plate in a first position relative to said pipette plate wherein said elastic membrane is engaged by said bosses with minimal tension and a second position wherein the bosses on said retaining plate and said pipette plate clamp said elastic membrane under tension with a portion of said elastic membrane extending into each of said pipettes barrels. The foregoing assembly can be sterilized and sealed within a suitable overwrap for sale as a testing kit for use with a plunger plate having a plurality of downwardly extending pins on the under surface thereof which are adapted to extend through said apertures in said retaining plate to engage said membrane to move said membrane downwardly and upwardly within said pipette to draw a predetermined quantity of a liquid into each pipette. Since the pins of the plunger plate do not contact the pipettes or liquid therein, it is not necessary for the plunger plate and pins to be sterilized and therefore the plunger plate can be used repeatedly while the kit may be suitably disposed of after a single use.

The present invention also contemplates the packaging of a plunger plate with each kit which contains sufficient elements for carrying out a simultaneous multiple liquid transfer. The length of the pins determines the amount of liquid to be transferred provided the plunger plate is pressed into engagement with the retaining plate.

The foregoing and other objects, features and advantages of the invention will be apparent from the following more particular description of preferred embodiments of the invention as illustrated in the accompanying drawings.

DETAILED DESCRIPTION OF THE INVENTION

Figure 1:
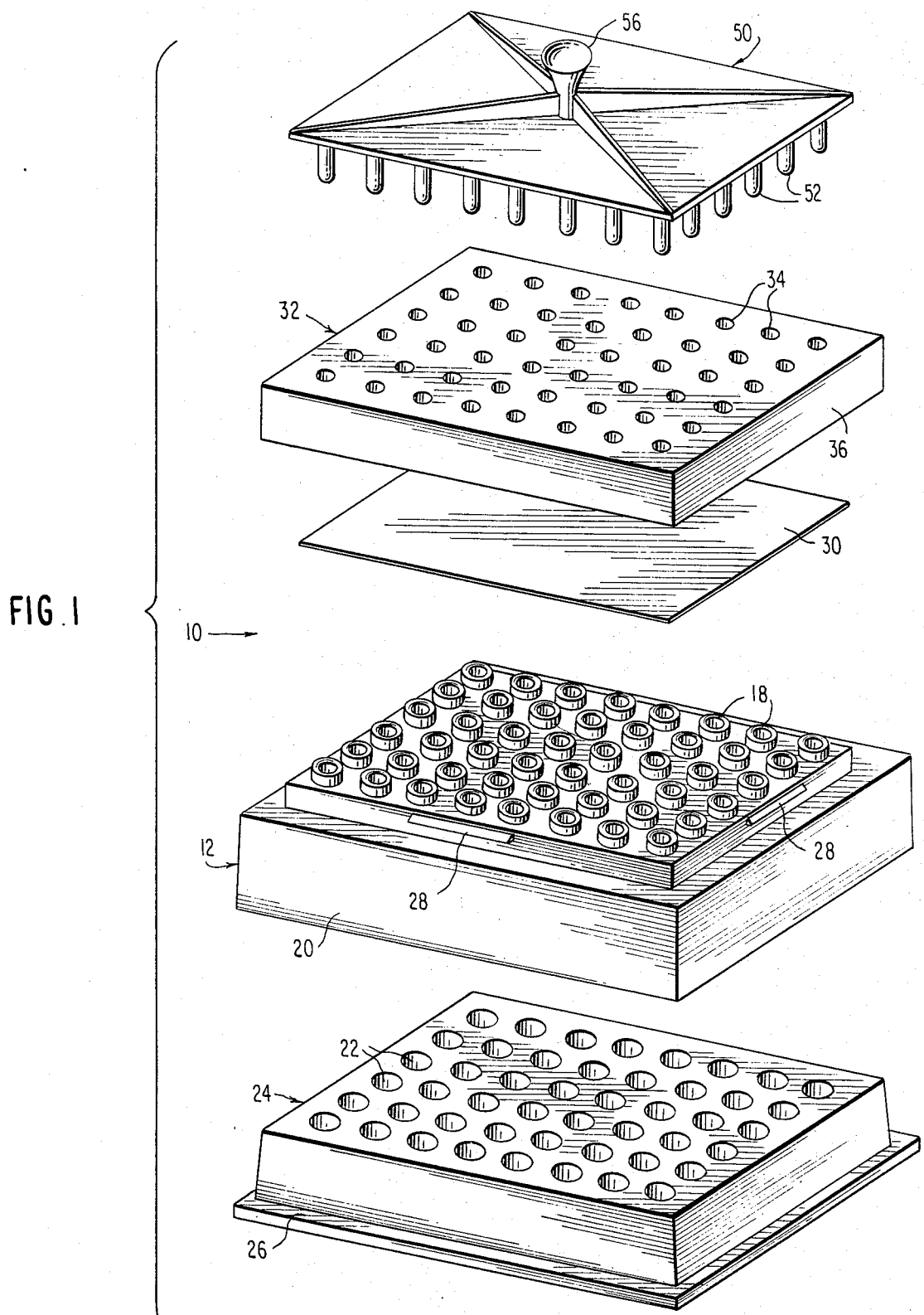
FIG. 1 is an exploded view of the various elements of the liquid transfer device according to the present application in alignment with a microtube tray.
Figure 3:
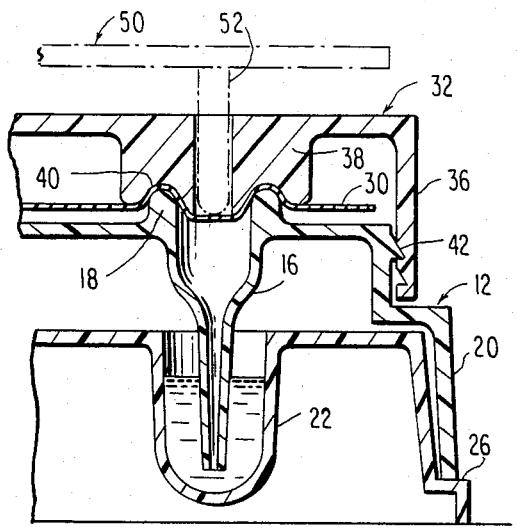
FIG. 3 is a partial sectional view with the retainer plate, elastic membrane and pipette plate assembled in a second position with the membrane stretched under tension in the upper end of a pipette with the plunger assembly and microtube tray positioned preparatory to withdrawing a liquid sample from the microtube tray.
Figure 4:
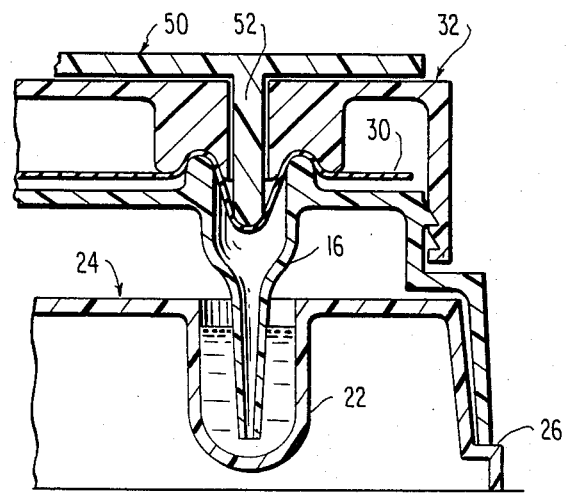
FIG. 4 is a view similar to FIG. 3 wherein the plunger assembly has been depressed to stretch the membrane further into the pipette to expel air from the pipette prior to drawing a quantity of liquid into the pipette.

The liquid transfer device 10 as shown in FIG. 1 is comprised of a one-piece molded plastic pipette plate assembly 12 having a plurality of apertures extending therethrough with a pipette 16 extending downwardly in alignment with each aperture 14 and an annular upstanding boss 18 surrounding each aperture 14. The pipette plate is provided with a downwardly extending flange 20 extending about the periphery thereof for supporting the lower ends of the pipettes 16 at a predetermined position within each well 22 of a conventional microtube tray 24. Conventional microtube trays 24 are generally provided with a peripheral base flange 26 upon which the lower edge of the flange 20 on the pipette plate will rest to position the lower end of each pipette in each well 22 as best seen in FIGS. 3 and 4. A laterally projecting flange 28 is provided on each side of the pipette plate with the lower surface of the flange 28 extending perpendicular to the side of the pipette plate and the upper surface of the flange sloping downwardly and outwardly from the side of the pipette plate so that each flange 28 has a substantially triangular cross-sectional configuration.

Figure 2:
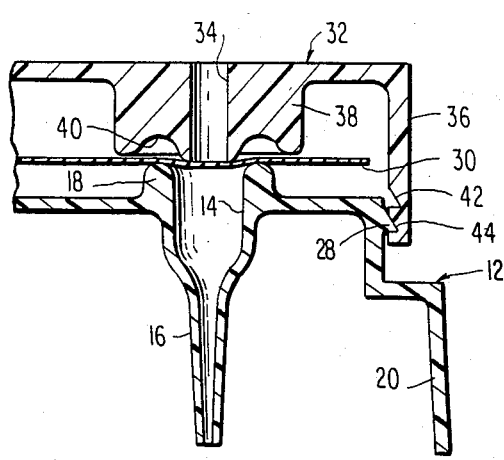
FIG. 2 is a partial sectional view showing the relationship of the retaining plate, elastic membrane and pipette plate in a first position suitable for sale and storage with the membrane under minimal tension.

A substantially rectilinear elastic membrane 30 of latex or any other suitable material is adapted to rest on the upper surface of each boss 18. A retainer plate 32 is provided with a plurality of apertures 34 extending through the flat upper surface and a downwardly depending flange 36 extending about the entire periphery of the plate. The dimensions of the elastic membrane 30 are such that the membrane lies within the downwardly depending flanges 36 on the retaining plate 32 while still covering all of the raised annular bosses 18 on the pipette plate. As best seen in FIG. 2, an annular downwardly extending boss 38 surrounds each aperture 34 and in turn is provided with an annular groove 40 in the lower surface thereof extending about the aperture 34.

The annular groove 40 surrounding each aperture 34 is disposed in alignment with each upstanding annular boss 18 on the pipette plate. Each downwardly extending flange 36 is provided with two notches 42 and 44 on the inner surface thereof adjacent the bottom edge of the flange. The notches 42 and 44 have a configuration complementary to the projections 28 on the sides of the pipette plate 12. While projections 28 have only been shown on two sides of the pipette plate 12, it is contemplated that similar projections could be provided on the other two sides of the pipette plate. It is also possible to only have two such projections on opposite sides of the pipette plate.

With the elastic membrane 30 resting on the raised annular bosses 18 of the pipette plate 12, the retaining plate 32 is lowered over the pipette plate until the projections 28 snap into the lowermost notch 44 as illustrated in FIG. 2. In this position, the membrane 30 is pressed a short distance into each pipette aperture thereby placing the elastic membrane under slight tension at each pipette location. This tension is sufficient to hold the membrane 30 in place during shipment of the assembly or testing kit which is comprised of the retaining plate, elastic membrane and pipette plate. This assembly can be sold as a testing kit in the manner shown in FIG. 6 wherein the sterilized assembly is provided with an overwrap 46 of any suitable material. When it is desired to utilize the kit to carry out a testing procedure, it is only necessary to remove the wrapper 46 and press the retaining plate 32 downwardly relative to the pipette plate 12 so that the projections 28 on the pipette plate will snap into the uppermost recesses 42 on the interior surface of the flanges 36. In this position, the upstanding annular bosses 18 press the elastic membrane 30 into the annular recesses 40 on the bottom of the bosses 38 on the retaining plate 32. Thus, the membrane 30 will be pressed further into each pipette opening thereby tensioning the elastic membrane further and providing a tight seal around the upper edge of the barrel opening. The liquid transfer assembly comprised of the retaining plate 32, the membrane 30 and the pipette plate 12 can then be placed over a conventional microtube tray 24 as illustrated in FIG. 3 whereby the lower end of each pipette 16 will extend a predetermined distance into each well 22 of the microtube tray 24. Alternatively, the liquid transfer assembly could be placed over a tray having a single large recess therein adapted to accommodate all of the pipettes 16. Thus, the liquid transfer assembly can then be used to transfer liquid from the single recess tray to each individual well of a microtube tray.

Figure 5:
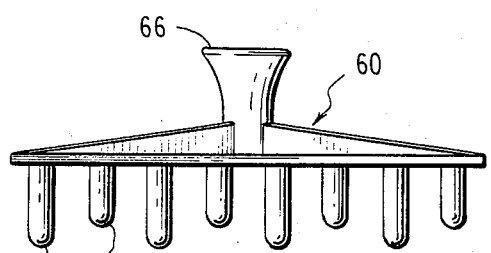
FIG. 5 illustrates a modified form of plunger assembly wherein the depending pins are of varying lengths for transferring different predetermined quantities of liquid.

In order to transfer liquid, the pins 52 of the plunger member are inserted into each of the apertures 34 in the retaining plate 32 into light engagement with the membrane 30 as shown in FIG. 3. Upon depression of the plunger member 50 into engagement with the upper surface of the retaining plate 32 as shown in FIG. 4, the pins 52 will push the elastic membrane 30 further into the passages of the pipettes 16 thereby forcing air from the lower end of the pipettes 16. Upon release of the plunger member 50, the elastic force of the membrane 30 will move the plunger member 50 upwardly to the position shown in FIG. 3 thereby drawing up a predetermined quantity of liquid into each barrel. As shown in FIG. 1, all of the pins 52 on the plunger plate 50 are of the same length and therefore the same amount of liquid will be drawn up into each of the barrels 16. By varying the length of the pins 52, the amount of liquid drawn up can be varied. While generally all the pins on a single plate are of the same length, it is also possible to provide pins of varying lengths on the plunger plate 60 in FIG. 5. The pins 62 are longer than the pins 64 and therefore those barrels associated with the pins 62 would transfer a larger quantity of liquid than the pipettes associated with the shorter pins 64. The plunger plates 50 and 60 are provided with operating handles 56 and 66, respectively, as well as reinforcing ribs. The configuration of the operating handles and the reinforcing ribs can be varied.

Figure 6:
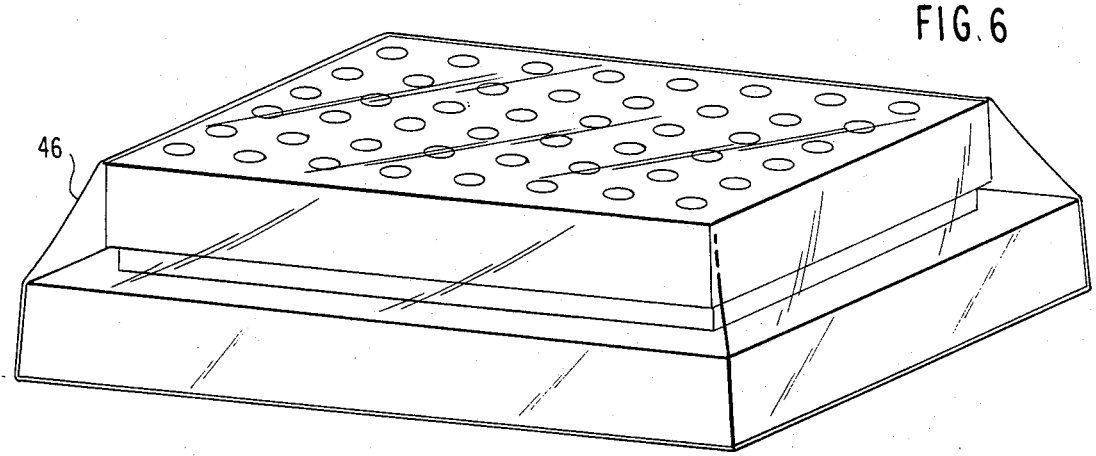
FIG. 6 is a perspective view showing the sterile wrapped testing kit comprised of a pipette plate, elastic membrane and retainer plate.

In actual practice, a large number of the testing kits as shown in FIG. 6 could be packaged in a single container along with two or three plunger plates each of which is provided with a set of pins of a different length. Therefore, during a particular testing operation, it is only necessary to unwrap a single testing kit and select the appropriate plunger member to transfer the desired amount of liquid. It is also contemplated that the plunger plate could also be packaged as a kit with the pipette plate, elastic membrane and retaining plate and wrapped as a single sterile unit. In such a situation, removable blocks could be placed between the plunger plate 50 and the upper surface of the retaining plate 32 as shown in FIG. 3 to prevent the pins 52 from pressing on the elastic membrane 30.

The individual three piece kits, each comprised of a pipette plate, a membrane and a retaining plate, can also be utilized with a mechanically operated device having a movable arm or piston upon which a plunger could be detachably secured. The movable arm or piston may be manually operated or motor driven and the extent of movement of the arm or piston may be varied to vary the distance the pins on the plunger plate will penetrate into the barrel plate thereby varying the amount of fluid transferred.

While the invention has been particularly shown and described with reference to preferred embodiments thereof, it will be understood by those in the art that the foregoing and other changes in form and detail may be made therein without departing from the spirit and scope of the invention.

What is claimed is:

1. A liquid transfer device comprising pipette plate means having a plurality of apertures extending therethrough, an upstanding annular boss extending about each aperture on the upper surface of the pipette plate means, a plurality of hollow pipette members secured to the undersurface of said pipette plate means with each hollow pipette member aligned with a respective aperture in said pipette plate means and downwardly extending support means, an elastic membrane covering each aperture in said pipette plate means and disposed in engagement with each upstanding annular boss and retaining plate means having a plurality of pin receiving apertures extending therethrough with a downwardly protruding boss surrounding each aperture in said retaining plate means and means for securing said pipette plate means and said retaining plate means together with the respective apertures in each plate disposed in alignment with each other and with said downwardly protruding bosses extending into the respective upstanding bosses on said pipette plate means to press said membrane into each aperture in said pipette plate means under tension to provide a liquid-tight seal about each aperture.

2. A liquid transfer device as set forth in claim 1 further comprising plunger plate means having a plurality of pins projecting from the undersurface thereof adapted to be inserted into respective apertures in said retaining plate means for engagement with said elastic membrane to press said elastic membrane into each pipette member.

3. A liquid transfer device as set forth in claim 1 further comprising package means for sealing said pipette plate means, said membrane, and said retaining plate means in a sterile condition.

4. A liquid transfer device as set forth in claim 2 further comprising package means for sealing said pipette plate means, said membrane, said retaining plate means and said plunger plate means in a sterile condition.

* * * * *